US00PP31056P2

(12) United States Plant Patent
Koppe

(10) Patent No.: US PP31,056 P2
(45) Date of Patent: Nov. 12, 2019

(54) ***BEGONIA* PLANT NAMED 'KRILOGO01'**

(50) Latin Name: ***Begonia* x *hiemalis***
Varietal Denomination: KRILOGO01

(71) Applicant: Lubbertus H. Koppe, Putten (NL)

(72) Inventor: Lubbertus H. Koppe, Putten (NL)

(73) Assignee: KOPPE ROYALTY B.V., Putten (NL)

( * ) Notice: Subject to any disclaimer, the term of this patent is extended or adjusted under 35 U.S.C. 154(b) by 0 days.

(21) Appl. No.: 16/350,337

(22) Filed: Nov. 2, 2018

(51) Int. Cl.
*A01H 5/02* (2018.01)
*A01H 6/18* (2018.01)

(52) U.S. Cl.
USPC ..... Plt./347

(58) Field of Classification Search
USPC ..... Plt./347
CPC ..... A01H 5/02; A01H 6/18
See application file for complete search history.

(56) References Cited

PUBLICATIONS

Pluto Plant Variety Database May 25, 2019. p. 1.*

* cited by examiner

*Primary Examiner* — Annette H Para
(74) *Attorney, Agent, or Firm* — C. A. Whealy

(57) ABSTRACT

A new and distinct cultivar of *Begonia* plant named 'KRILOGO01' characterized by its upright to outwardly spreading and mounded plant habit; moderately vigorous growth habit; freely branching habit; dark green-colored leaves; freely flowering habit; double-type flowers that are orange in color and held above and beyond the foliar plane; and excellent postproduction longevity.

2 Drawing Sheets

Botanical designation: *Begonia* x *hiemalis*.
Cultivar denomination: 'KRILOGO01'.

BACKGROUND OF THE INVENTION

The present invention relates to a new and distinct cultivar of *Begonia* plant, botanically known as *Begonia* x *hiemalis*, commercially referred to as an Elatior *Begonia* and hereinafter referred to by the name 'KRILOGO01'.

The new *Begonia* plant is a product of a planned breeding program conducted by the Inventor in Ermelo, The Netherlands. The objective of the breeding program is to create new freely-branching *Begonia* plants with excellent postproduction longevity and attractive flower color.

The new *Begonia* plant is a naturally-occurring whole plant mutation of *Begonia* x *hiemalis* 'Reins', disclosed in U.S. Plant Pat. No. 19,336. The new *Begonia* plant was discovered and selected by the Inventor as a single flowering plant from within a population of plants of 'Reina' in a controlled greenhouse environment in Ermelo, The Netherlands in June, 2016. Asexual reproduction of the new *Begonia* plant by terminal vegetative cuttings taken in a controlled greenhouse environment in Ermelo, The Netherlands since September, 2016 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'KRILOGO01'. These characteristics in combination distinguish 'KRILOGO01' as a new and distinct *Begonia* plant:

1. Upright to outwardly spreading and mounded plant habit.
2. Moderately vigorous growth habit.
3. Freely branching habit.
4. Dark green-colored leaves.
5. Freely flowering habit.
6. Double-type flowers that are orange in color and held above and beyond the foliar plane.
7. Excellent postproduction longevity.

Plants of the new *Begonia* differ primarily from plants of the mutation parent, 'Reina', primarily in flower color as plants of 'Reina' have darker orange-colored flowers than plants of the new *Begonia*.

Plants of the new *Begonia* can be compared to plants of *Begonia* x *hiemalis* 'Batik', not patented. In side-by-side comparisons conducted in Ermelo, The Netherlands, plants of the new *Begonia* differ primarily from plants of 'Batik' in the following characteristics:

1. Plants of the new *Begonia* have larger flowers than plants of 'Batik'.
2. Plants of the new *Begonia* have double-type flowers whereas plants of 'Batik' have single-type flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical plant of 'KRILOGO01' grown in a container.

The photograph on the second sheet are close up views of the upper (right) and lower (left) surfaces of typical leaves and flowers of 'KRILOGO01', and in the center of the photograph is a close-up view of typical flower buds.

DETAILED BOTANICAL DESCRIPTION

The aforementioned photographs and following observations and measurements describe plants grown during the spring and early summer in 12-cm containers in a glass-covered greenhouse in Ermelo, The Netherlands and under cultural practices typical of commercial *Begonia* production. During the production of the plants, day temperatures averaged 20° C. and night temperatures averaged 18° C. Plants were twelve weeks old when the photographs and description were taken. In the following description, color references are made to The Royal Horticultural Society Colour Chart, 2015 Edition, except where general terms of ordinary dictionary significance are used.

Botanical classification: *Begonia* x *hiemalis* 'KRILOGO01'.

Parentage: Naturally-occurring whole plant mutation of *Begonia* x *hiemalis* 'Reina', disclosed in U.S. Plant Pat. No. 19,336.

Propagation:

*Type*.—By terminal vegetative cuttings.

*Time to initiate roots, summer and winter*.—About 20 days at temperatures about 20° C.

*Time to produce a rooted young plant, summer and winter*.—About five weeks at temperatures about 20° C.

*Root description*.—Fine, fibrous; typically white to orange brown in color, actual color of the roots is dependent on substrate composition, water quality, fertilizer type and formulation, substrate temperature and physiological age of roots.

*Rooting habit*.—Freely branching; medium density; plants of the new *Begonia* have not been observed to form tubers.

Plant description:

*Plant habit and form*.—Upright to outwardly spreading and mounded plant habit; overall plant shape, broadly obovate to nearly globular.

*Growth habit*.—Moderately vigorous growth habit and moderate growth rate; suitable for 12-cm and larger containers; under optimal environmental and cultural conditions, usually about nine weeks are required to produce proportional plants in 12-cm containers.

*Branching habit*.—Freely branching with about three primary branches each with about two secondary branches developing per plant.

*Plant height, soil level to top of foliar plane*.—About 24.9 cm.

*Plant height, soil level to top of floral plane*.—About 29.5 cm.

*Plant width*.—About 37.6 cm.

*Lateral branches*.—Length: About 11.2 cm. Diameter: About 9.5 mm to 10 mm. Internode length: About 3.1 cm. Strength: Moderately strong. Aspect: About 50° from vertical. Texture and luster: Moderately pubescent; glossy. Color, developing: Close to 144A. Color, developed: Close to 146A to 146B. Lenticels: None observed on plants of the new *Begonia* to date.

*Leaves*.—Arrangement: Alternate, simple. Length: About 15.8 cm. Width: About 12 cm. Shape: Ovate, asymmetrical. Apex: Acute. Base: Truncate to hastate with cordate tendencies; lobes not imbricate. Margin: Serrate to dentate; strongly and coarsely undulate. Texture and luster, upper surface: Smooth, glabrous; slightly velvety; slightly glossy. Texture and luster, lower surface: Sparsely pubescent along venation; moderately glossy. Venation pattern: Laciniate. Color: Developing leaves, upper surface: Close to between 141A and 146A. Developing leaves, lower surface: Close to 138B. Fully expanded leaves, upper surface: Darker than between NN137A and 147A; venation, close to 144A. Fully expanded leaves, lower surface: Close to 148B; venation, close to 146C to 146D. Petioles: Length: About 8 cm. Diameter: About 7 mm. Strength: Low, flexible. Texture and luster, upper and lower surfaces: Sparsely pubescent; moderately glossy. Color, upper surface: Close to 146C to 146D; developed petioles, tinged with close to 179B; distally, small spot, close to 180C. Color, lower surface: Close to 146D. Stipules: Length: About 1.5 cm. Width: About 1.5 cm. Shape: Broadly ovate. Apex: Bluntly acute. Base: Broadly cuneate. Margin: Entire to irregularly ciliate. Texture and luster, upper and lower surfaces: Smooth, glabrous; moderately glossy. Color, upper and lower surfaces: Close to 145B; venation, close to 146C.

Flower description:

*Flower appearance and flowering habit*.—Double-type rotate flowers with four tepals and numerous tepaloids; flowers arranged in axillary compound cymes; freely flowering habit with typically about nine flowers per cyme and about 170 flowers and flower buds developing per plant; many cymes in flower simultaneously; flowers positioned above and beyond the foliar plane and face upright to slightly outwardly; only male flower development has been observed to date on plants of the new *Begonia*.

*Natural flowering season*.—Plants begin flowering about five weeks after planting; plants will flower year round regardless of nyctoperiod, however plants flower earlier and more abundantly from spring into the autumn in The Netherlands.

*Postproduction longevity*.—Individual flowers last about ten days on the plant; flowers not persistent; excellent postproduction longevity, plants maintain good substance for about 40 days in an interior environment.

*Fragrance*.—None detected.

*Inflorescence height*.—About 9.6 cm.

*Inflorescence diameter*.—About 12.8 cm.

*Flowers*.—Shape: Rotate, double-type. Diameter: About 6.1 cm by 6.1 cm. Depth (height): About 2.3 cm.

*Flower buds*.—Length: About 2 cm. Diameter: About 0.6 cm to 2.1 cm. Shape: Nearly circular, flattened. Texture and luster: Glabrous; slightly velvety; slightly glossy. Color: Close to 149D; towards the apex, close to 43C.

*Tepals*.—Quantity and arrangement per flower: Usually about four per flower arranged in two whorls. Length, lower tepals: About 3.4 cm. Width, lower tepals: About 4.5 cm. Length, upper tepals: About 2.5 cm. Width, upper tepals: About 3 cm. Shape, all tepals: Reniform. Apex, all tepals: Rounded. Base, all tepals: Reniform. Margin, all tepals: Entire; not undulate. Texture and luster, upper and lower surfaces, all tepals: Smooth, glabrous; moderately velvety; matte. Color, lower tepals: When opening, upper surface: Close to 25C; towards the base, close to 23B. When opening, lower surface: Close to 40C; towards the margins, close to 32C. Fully opened, upper surface: Close to 24B; towards the base, close to 15C; venation, similar to lamina color; color does not change with development. Fully opened, lower surface: Close to 44D; towards the margins, close to 35B; venation, close to 22A; color does not change with development. Color, upper tepals: When opening, upper surface: Close to 25A; towards the base, close to 25B. When opening, lower surface: Close to 28C. Fully opened, upper surface: Close to 25A; towards the margins, close to N25A to N25B; towards the base, close to 25B; venation, similar to lamina color; color does not change with development. Fully opened, lower surface: Close to 31B; towards the margins, close to 30C; venation, close to 22A; color does not change with development.

*Tepaloids*.—Quantity and arrangement per flower: Typically about 34 per flower clustered at the center of the flower. Length: About 0.9 cm to 2.2 cm. Width: About 0.3 cm to 1.6 cm. Shape: Obovate. Apex: Obtuse to broadly and shallowly emarginate. Base: Attenuate. Margin: Entire; slightly undulate. Texture and luster, upper and lower surfaces: Smooth, glabrous; moderately velvety; matte. Color: When opening, upper surface: Close to 25A; towards the margins and apex, close to 32A. When opening, lower surface: Close to 35B; towards the margins and apex, close to 40C. Fully opened, upper surface: Close to 28B; towards the apex, close to 28A; towards the base, close to 25B; venation, similar to lamina color; color does not change with development. Fully opened, lower surface: Close to 29B; towards the margins and apex, close to 30B to 30C; venation, close to 26A; color does not change with development.

*Peduncles*.—Length: About 7.8 cm. Diameter: About 4 mm to 5.5 mm. Strength: Moderately strong. Aspect: About 40° from lateral branch axis. Texture and luster: Smooth, glabrous; moderately glossy. Color: Close to 144B.

*Pedicels*.—Length: About 3 cm. Diameter: About 2 mm. Strength: Moderately strong. Aspect: About 40° from peduncle axis. Texture and luster: Smooth, glabrous; glossy. Color: Close to 31C.

*Flower bracts*.—Quantity per flower: Two. Length: About 1.4 cm. Width: About 1.6 cm. Shape: Broadly ovate. Apex: Bluntly acute. Base: Broadly cuneate. Margin: Entire to finely ciliate. Texture and luster, upper and lower surfaces: Smooth; glabrous; slightly glossy. Color, upper and lower surfaces: Close to 145B; towards the apex, close to 179B; venation, close to 143B.

*Reproductive organs*.—Stamens transformed into tepaloids; flowers are sterile. Female flower development has not been observed on plants of the new *Begonia* to date; no seed nor fruit production has been observed to date.

Disease & pest resistance: Resistance to pathogens and pests common to *Begonia* plants has not been observed on plants of the new *Begonia* to date.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'KRILOGO01' as illustrated and described.

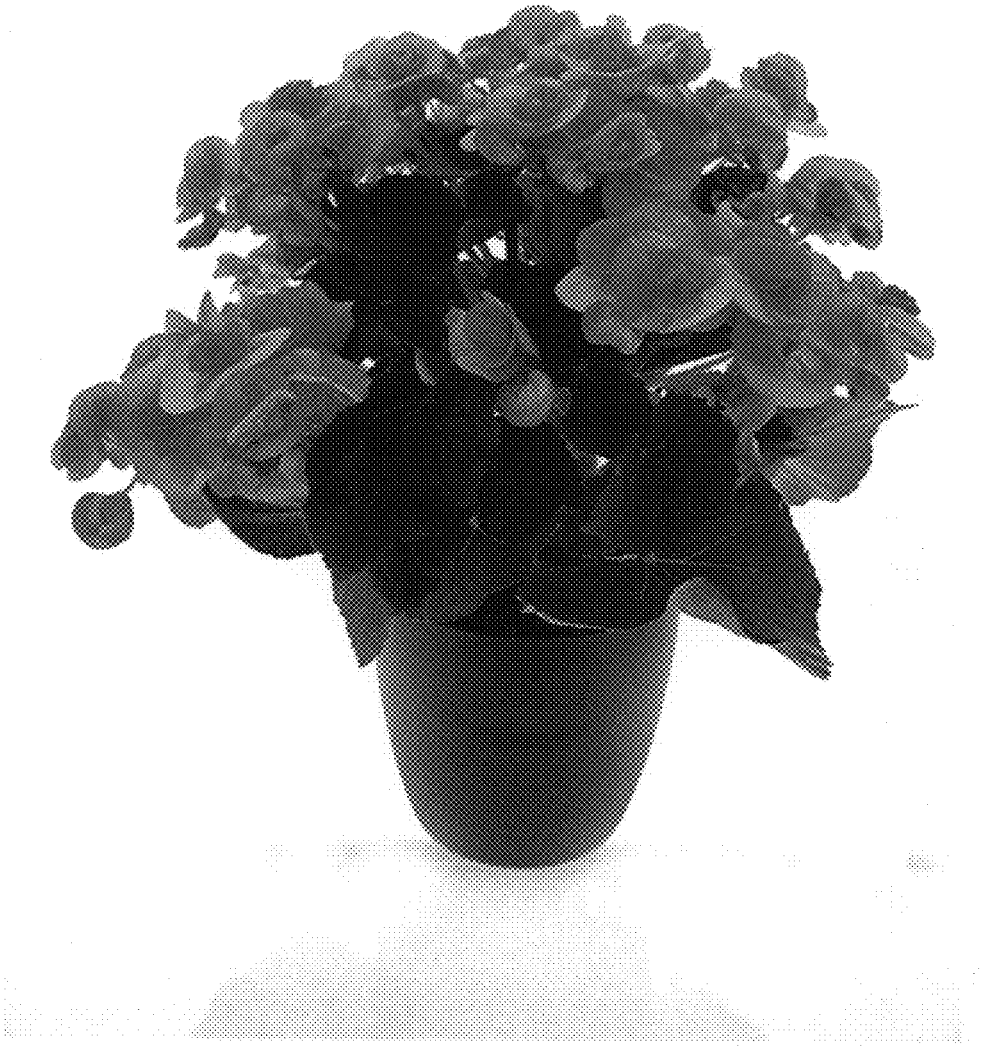

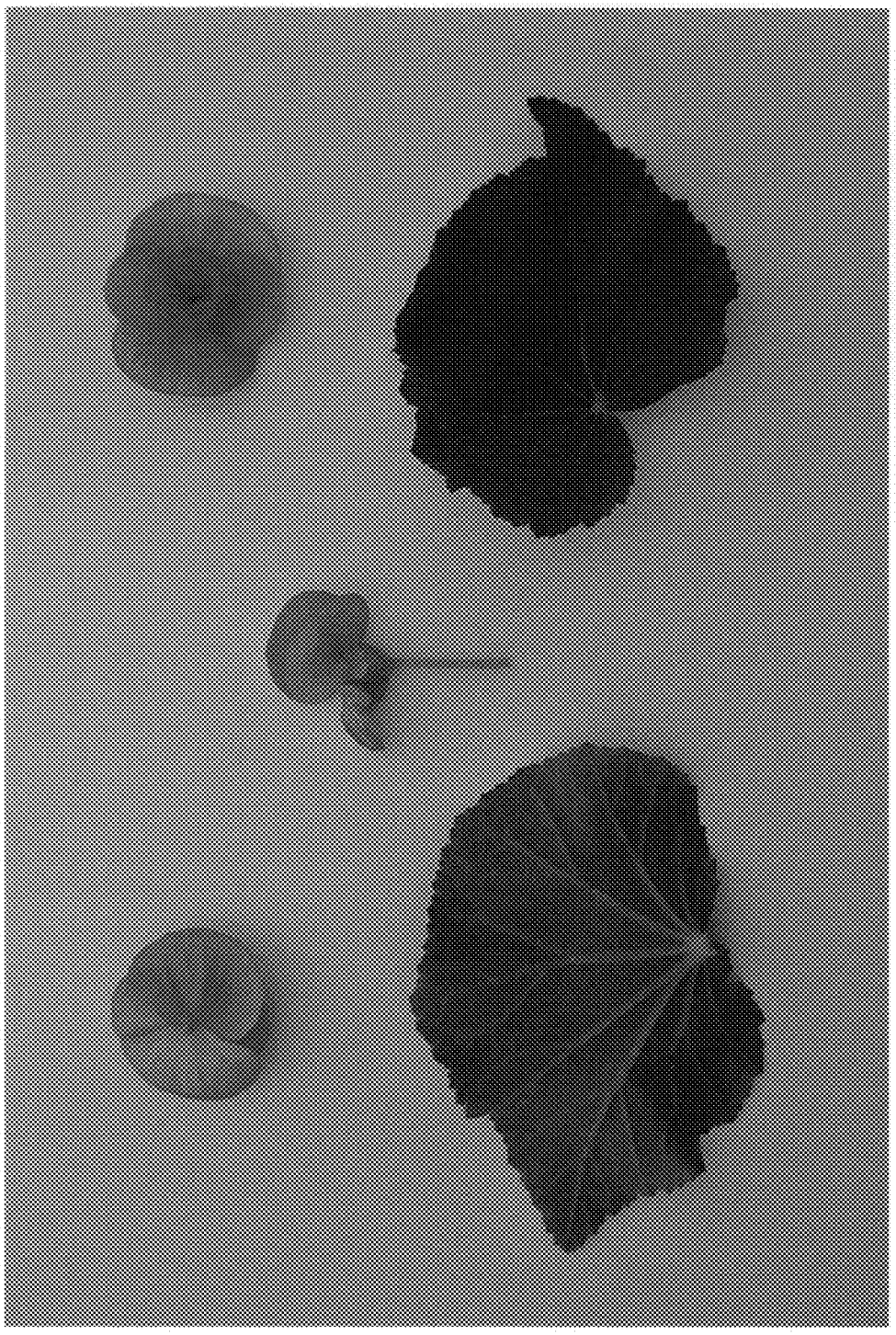

* * * * *